United States Patent [19]

Rosenberg et al.

[11] Patent Number: 5,276,128
[45] Date of Patent: Jan. 4, 1994

[54] SALTS OF POLYBENZAZOLE MONOMERS AND THEIR USE

[75] Inventors: Steven Rosenberg; Richard C. Krauss, both of Midland, Mich.; Ming-Biann Liu, Clayton, Calif.; Luke R. Kleiss, Lisle, Ill.

[73] Assignee: The Dow Chemical Company, Midland, Mich.

[21] Appl. No.: 780,493

[22] Filed: Oct. 22, 1991

[51] Int. Cl.$^5$ .............................. C08G 63/00
[52] U.S. Cl. .................... 528/184; 528/185; 528/172; 528/179; 528/207; 528/208; 528/210; 528/211
[58] Field of Search ............... 528/186, 185, 172, 179, 528/251, 258, 210, 211

[56] References Cited

U.S. PATENT DOCUMENTS

| | | | |
|---|---|---|---|
| 4,533,693 | 8/1985 | Wolfe et al. | 524/417 |
| 4,766,244 | 8/1988 | Lysenko | 564/418 |
| 4,806,688 | 2/1989 | Inbasekaran et al. | 564/443 |
| 4,912,246 | 3/1990 | Lysenko et al. | 558/269 |
| 4,945,153 | 7/1990 | Nishino | 528/337 |
| 4,948,867 | 8/1990 | Nishino | 528/337 |
| 4,982,001 | 1/1991 | Lysenko | 564/418 |
| 5,001,265 | 3/1991 | Liu et al. | 564/418 |
| 5,089,591 | 2/1992 | Gregory et al. | 528/184 |

FOREIGN PATENT DOCUMENTS 256534 10/1989 Japan.
9006960 6/1990 PCT Int'l Appl..

OTHER PUBLICATIONS

11 Encyclopedia Poly. Sci. & Eng., *Polybenzothiazoles and Polybenzoxazoles*, 601(J. Wiley & Sons 1989).
Ledbetter et al., *An Integrated Laboratory Process for Preparing Rigid Rod Fibers from the Monomers*, The Materials Science and Engineering of Rigid Rod Polymers, 253-64 (Materials Research Society 1989).

*Primary Examiner*—John Kight, III
*Assistant Examiner*—Dvc Truong

[57] ABSTRACT

Salts that contain AA-PBZ monomer ions and BB-PBZ monomer ions can be precipitated from an aqueous solution by contacting soluble salts of the monomers in an aqueous solution. The monomer salt can be polymerized by ordinary techniques to form polybenzazole polymers without the need for devolatilization and with very accurate stoichiometric control.

24 Claims, No Drawings

SALTS OF POLYBENZAZOLE MONOMERS AND THEIR USE

BACKGROUND OF THE INVENTION

The present invention relates to monomers that are useful to make polybenzazole polymers, processes to make those monomers and methods to use those monomers.

Polybenzazole polymers are synthesized by the reaction of AA-PBZ monomers with BB-PBZ monomers. The AA-PBZ monomer (which is sometimes also referred to as a dicarboxylic acid monomer) contains two electron-deficient carbon groups linked by a divalent organic moiety. It is frequently illustrated by Formula 1:

$$Q\text{-}DM\text{-}Q \qquad (1)$$

wherein each Q is an electron-deficient carbon group and DM is a divalent organic moiety.

The BB-PBZ monomer (which is sometimes also referred to as a diamino-dihydroxy monomer or a diamino-dithio monomer) contains an aromatic group having two o-amino-basic moieties bonded to it. Each o-amino-basic moiety contains a first primary amine group bonded to the aromatic group and a hydroxyl, thiol or primary or secondary amine group bonded to the aromatic group in the ortho position with respect to the first primary amine group. The BB-PBZ monomer is ordinarily represented by Formula 2:

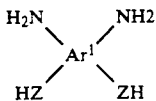

wherein $Ar^1$ is the aromatic group, each Z is —O—, —S—, or —NR—, and R is a hydrogen atom, an alkyl group or an aromatic group. The representation of bonds to an aromatic group without indicating position, as in Formula 2, indicates that the amine groups and —ZH groups may be in either cis- or trans- position with respect to each other. Each amine group must be ortho to one of the —ZH groups.

The BB-PBZ monomer is highly susceptible to oxidation when it is in a free-base state. It is ordinarily stored and handled as a hydrogen chloride salt, which is more stable. The hydrogen chloride is removed in a devolatilization step after the BB-PBZ monomer is dissolved in a polymerization solvent but prior to polymerization. The devolatilization step is time-consuming, but necessary because the hydrogen chloride interferes with polymerization of the monomer. It would be desirable to find new monomers that eliminate the need for the devolatilization step.

The monomers are usually polymerized in a dehydrating and non-oxidizing acid mixture. Proper stoichiometry is very important in the polymerization, since the reaction is a condensation polymerization. A small excess of BB-PBZ monomer can prevent the reaction from producing high-molecular weight polybenzazole polymer. It would be desirable to find new monomers that are simple to load in stoichiometric quantities.

SUMMARY OF THE INVENTION

One aspect of the present invention is a solid AA-PBZ monomer/BB-PBZ monomer salt comprising:
(1) protonated BB-PBZ monomer cations; and
(2) AA-PBZ monomer anions.

A second aspect of the present invention is a process to make an AA-PBZ monomer/BB-PBZ monomer salt of the present invention comprising the step of contacting an aqueous-soluble AA-PBZ monomer salt with an aqueous-soluble BB-PBZ monomer salt in an aqueous solution under conditions such that the AA-PBZ monomer/BB-PBZ monomer salt precipitates.

A third aspect of the present invention is a method of using an AA-PBZ monomer/BB-PBZ monomer salt of the present invention comprising the steps of:
(1) mixing a salt that contains both AA-PBZ monomer ions and BB-PBZ monomer ions with a solvent that is suitable for making polybenzazole polymers to form a polymerization mixture; and
(2) reacting the monomers in the polymerization mixture under conditions such that a mixture containing a polybenzazole polymer is formed.

The salt of the present invention can be made by the process of the present invention and used according to the method of the present invention to form polybenzazole polymers. Salts of the present invention do not ordinarily require devolatilization. Moreover, they are preferably in about a homogeneous 1:1 stoichiometry, so that good stoichiometry is inherently obtained by mixing the salt in the polymerization mixture.

DETAILED DESCRIPTION OF THE INVENTION

The present invention uses AA-PBZ monomers. AA-PBZ monomers are described previously and are well-known in the art. Several preferred examples are described in Wolfe et al., U.S. Pat. No. 4,533,693 (Aug. 5, 1985) at Col. 24-32, which is incorporated herein by reference. The electron-deficient carbon groups (Q) in the AA-PBZ monomers should be carboxylate salts or other groups that are readily converted to carboxylate salts, such as carboxylic acid groups. The counter-ion for the carboxylate salt is selected so that the monomer is soluble in an aqueous solution. The counter-ion is preferably an alkali metal, such as sodium or potassium. The divalent moiety (DM) is preferably an alkyl group or an aromatic group, and is more preferably an aromatic group.

The aromatic group in the AA-PBZ monomer may be a multi-ring fused or unfused structure (such as naphthalene, biphenylene or diphenylene ether), but it is preferably a single ring such as phenylene. The aromatic group may be a nitrogen heterocycle (such as pyridine) but it is preferably carbocyclic and more preferably hydrocarbyl. It is preferably selected such that the AA-PBZ monomer is suitable to form lyotropic liquid crystalline polymers; i.e. the aromatic group is para ordered (such as 1,4-naphthalene or 4,4'-biphenylene). Preferred examples of AA-PBZ monomers are terephthalic acid and bis-(4-benzoic acid) or salts thereof. Other examples which may be used include isophthalic acid; oxy-bis-(benzoic acid); hexafluoroisopropylidene-bis-(benzoic acid); isopropylidene-bis-(benzoic acid); 1,1,3-trimethyl-3-phenylindan-4',5-dicarboxylic acid and salts thereof.

The present invention also uses BB-PBZ monomers. BB-PBZ monomers are described previously and are well-known in the art. Several examples are described as hydrogen chloride salts in Col. 17-24 of U.S. Pat. No. 4,533,693, which is incorporated herein by reference. The BB-PBZ monomers are preferably suitable to form a polybenzoxazole polymer (Z=—O—) or a polybenzothiazole polymer (Z=—S—), and are more preferably suitable to form a polybenzoxazole polymer. The aromatic group (Ar$^1$) may also be a single ring or multi-ring group and may be heterocyclic or carbocyclic. It is preferably represented by either of Formulae 3(a) or (b):

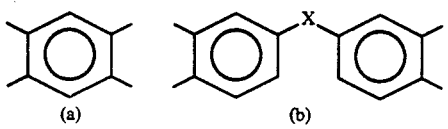

and is more preferably represented by Formula 3(a), wherein X is nil, an oxygen atom, a carbonyl group, a sulfonyl group, an alkyl group, or a haloalkyl group. The BB-PBZ monomers are preferably suitable to form a lyotropic liquid crystalline polymer. Examples of preferred BB-PBZ monomers include 4,6-diaminoresorcinol, 2,5-diaminohydroquinone, 2,4-diamino-1,5-dithiobenzene and 2,5-diamino-1,4-dithiobenzene. Other examples of BB-PBZ monomers include sulfonyl-bis-(o-aminophenol), oxy-bis-(o-aminophenol), hexafluoroisopropylidene-bis-(o-aminophenol) and variations in which the —OH groups are replaced with —SH groups. The BB-monomer should be in the form of a salt that is soluble in an aqueous solution, such as a phosphate salt or a hydrogen halide salt—preferably hydrogen chloride.

The AA-PBZ monomer salt and the BB-PBZ monomer salt are contacted in an aqueous solution under conditions such that a salt containing both AA-PBZ monomer and BB-PBZ monomer is formed. This can be accomplished simply by forming a first aqueous solution that contains a dissolved AA-PBZ monomer salt and mixing it with a second aqueous solution that contains a dissolved BB-PBZ monomer salt. It can also be accomplished by mixing the soluble salts together in a single solution. The temperature is not critical as long as the aqueous solution is liquid and the monomer is not adversely affected. It is preferably no more than about 100° C. and preferably at least about 0° C. For some purposes, it may be preferable to keep the temperature below about 60° C. to maintain monomer stability, but for other purposes it may be preferable to operate at a higher temperature, such as 90° C. or above, to grow larger crystals. The pressure is not critical, but is conveniently about ambient pressure. The atmosphere is preferably a non-oxidizing atmosphere, such as nitrogen or a noble gas.

The first solution can be made by adding a suitable AA-PBZ monomer, in which the electron-deficient carbon groups are carboxylic acids, (such a terephthalic acid) to an aqueous solution containing a base suitable to convert the acid groups to carboxylate salts. Exemplary bases include ammonium hydroxide alkali metal carbonates, alkali metal bicarbonates and alkali metal hydroxides. The alkali metal is preferably lithium, sodium or potassium and more preferably sodium. The concentration of AA-PBZ monomer in the solution chosen so that the desired AA-PBZ monomer/BB-PBZ monomer can precipitate in high yields. It is preferably at least about 0.05 molar, more preferably at least about 0.15 molar and most preferably at least about 0.2 molar. The preferred temperature ranges are similar to those previously described. The maximum concentration is governed by practical considerations, such as solubility, but is usually no more than about 1 molar.

The second solution can be made simply by dissolving a water-soluble salt of the BB-PBZ monomer in water. It should be maintained under the conditions previously described. The concentrations are preferably as described for the AA-PBZ monomer.

The two solutions are mixed together. The rate at which the solutions are mixed is preferably slow enough to avoid trapping inorganic counterions, such as phosphate or halide ions, in the crystals that are formed. The optimum rate will vary depending upon many factors, such as scale, equipment and conditions. It can readily be determined by a person of ordinary skill. The AA-PBZ monomer/BB-PBZ monomer salt precipitates from the aqueous solution rapidly under preferred conditions. It is preferably removed from the solution by known methods, such as filtering, and washed with water to remove residual counterions, such as phosphate or halide ions. The recovery is preferably at least about 95 percent, more preferably at least about 98 percent and most preferably at least about 99 percent.

The salt contains AA-PBZ monomer ions and BB-PBZ monomer ions. It preferably contains no more than 1 weight percent of volatile inorganic acids, such as hydrogen halide. For instance, the salt more preferably contains no more than about 1000 ppm halide ion by weight and most preferably contains no more than about 220 ppm halide ion by weight. Similar preferred limitations apply to phosphate ions and other inorganic counterions. The molar ratio of AA-PBZ monomers to BB-PBZ monomer in the salt is preferably about 1:1. The salt preferably contains no more than about a 5 mole percent excess of either monomer, and more preferably contains no more than about a 3 mole percent excess of either monomer. BB-PBZ monomers in the salt are protonated, so that they are preferably stable to at least brief exposure to air at about room temperature.

The monomer salt can be polymerized by ordinary techniques for polybenzazole polymerization. The reaction is typically carried out in an appropriate solvent, which is usually a non-oxidizing, dehydrating acid. Polyphosphoric acid or a mixture of methanesulfonic acid and a dehydrating agent such as $P_2O_5$ are the preferred solvents for the polymerization.

The concentration of $P_2O_5$ in polyphosphoric acid solvents has been described in numerous references, such as Wolfe, U.S. Pat. No. 4,533,693 (Aug. 5, 1985) at Col. 42–44; Sybert, U.S. Pat. No. 4,772,678 (Sep. 20, 1988) at Col. 39–40 and FIGS. 10–14; 16–18; and 11 Encyclopedia Poly. Sci. & Eng., *Polybenzothiazoles and Polybenzoxazoles*, at 611–619 (J. Wiley & Sons 1988), which are incorporated herein by reference. However, preferred salts of the present invention do not usually require devolatilization. Therefore, the concentration of $P_2O_5$ at the commencement of the reaction in a polyphosphoric acid may be at a level suitable for polymerization. For instance, the polyphosphoric acid preferably contains at least about 82 weight percent $P_2O_5$ and more preferably at least about 83 weight percent. The maximum concentration of $P_2O_5$, is limited by practical considerations, such as viscosity. It is usually no more than about 92 weight percent and more typically no more than about 90 weight percent. Such levels of P$_2$O$_5$ are preferable during the polymerization of the monomers. Because of polyphosphoric acid that contains high levels of P$_2$O$_5$ is highly viscous, it may be desirable to mix the salt into a polyphosphoric acid that contains lower levels of P$_2$O$_5$ and add additional P$_2$O$_5$ simultaneously with or subsequently to the salt.

The concentration of monomer salt in the reaction mixture should be high enough so that the resulting dope contains enough polymer to be processable. The final dope preferably contains at least about 7 weight percent polymer, more preferably at least about 10 weight percent polymer, and most preferably at least about 14 weight percent polymer. The maximum concentration is limited primarily by practical considerations, such as the viscosity of the dope. Dopes usually contain no more than about 20 weight percent lyotropic liquid crystalline polymer; more frequently no more than about 18 weight percent and most often no more than about 16 weight percent. The concentration and monomers are preferably selected so that the polymerization forms a liquid crystalline dope.

The reaction mixture is preferably agitated vigorously. It is viscous, and so equipment used to mix is preferably suitable for viscous materials, such as kneaders, extruders, press-mixers, etc. The reaction mixture is preferably reacted under high shear.

The reaction temperature may follow standard profiles, such as starting at about 100° C. or less and increasing the temperature over time to at least about 190° C. However, the AA-PBZ monomer/BB-PBZ monomer salt also permits a more rapid polymerization profile. When the halide content of the salt is relatively low (such as no more than about 200 ppm by weight), no devolatilization is necessary. The reaction may be commenced at a relatively high temperature. The commencing temperature is preferably at least about 140° C., more preferably at least about 150° C. and more preferably at least about 170° C. It is preferably no more than about 200° C., more preferably no more than about 190° C. and most preferably no more than about 180° C. The temperature is preferably raised as the reaction proceeds to a temperature of preferably at least about 170° C. and more preferably at least about 190° C. It is preferably no more than about 250° C., more preferably no more than about 230° C. and most preferably no more than about 210° C. The reaction can be completed to high molecular weight very quickly. With ordinary laboratory equipment, the reaction can proceed in less than 4 hours from monomer to polymer whose intrinsic viscosity is about 20-40 dL/g in methanesulfonic acid at about 25° C. It is anticipated that faster polymerization may be possible in optimized production scale equipment.

The polymerization may be practiced using known variations. For instance, monofunctional reagents may be added to the reaction mixture to cap the ends of the polymer chain and/or control molecular weight such as reagents described in Sybert et al., U.S. Pat. No. 4,772,678 (Sep. 20, 1988) at Col. 22-27, which is incorporated herein by reference. The reaction mixture may contain two or more different types of AA-PBZ monomer and/or BB-PBZ monomer to make copolymers. The mixture may also contain some AB-PBZ monomer, such as those described in Wolfe et al., U.S. Pat. No. 4,533,693 (Aug. 5, 1985) at Col. 32-35, which is incorporated herein by reference.

The polymerization preferably results in a dope containing polybenzazole polymer dissolved in a solvent acid as previously described. The dope can be used according to known and ordinary uses for polybenzazole dopes, such as spinning to make fibers or extruding to make films. The fibers and films are useful as structural materials.

The invention is further illustrated by the following working examples.

ILLUSTRATIVE EXAMPLES

The following examples are for illustrative purposes only, and should not be taken as limiting the scope of either the Claims or the Specification. Unless stated otherwise, all parts and percentages are by weight.

EXAMPLE 1

Diaminoresorcinol Terephthalate Salt

A first solution is made by dissolving 3.89 g of micronized terephthalic acid and 2.49 g of sodium carbonate in 50 ml of water at room temperature. The solids dissolve except for a few particles.

A second solution is made by dissolving 3.38 g of 4,6-diaminoresorcinol bis(hydrogen chloride) salt in 50 ml of water at room temperature under nitrogen atmosphere.

The first solution is added to the second solution dropwise through a filter paper over a period of 10 minutes. A 4,6-diaminoresorcinol terephthalate salt precipitates immediately. The salt is isolated and dried in a vacuum oven at 25° C., and 6.89 g is recovered. The salt is characterized by infrared spectroscopy, hydrogen and carbon[13] NMR and elemental analysis. All show it to be a salt of the 4,6-diaminoresorcinol and terephthalic acid. Elemental analysis shows that it contains 250-380 ppm of chlorine and 81-104 ppm sodium.

The salt is polymerized in a stirred resin kettle by: (1) mixing 10.27 g of salt, 27.9 g of polyphosphoric acid that contains 83.6 weight percent P$_2$O$_5$ and 10.6 g of P$_2$O$_5$ for one hour at 70° C.; (2) reacting for 22 hours at 150° C.; and (3) reacting for 30 hours at 200° C. The resulting polybenzoxazole polymer has a single point intrinsic viscosity of about 32 dL/g in methanesulfonic acid at 25° C.

EXAMPLE 2

Diaminoresorcinol Terephthalate Salt

The process to make salt of Example 1 is repeated, except that the quantities of 4,6-diaminoresorcinol bis(hydrogen chloride) (DAR) and terephthalic acid (TA) used are varied so that the ratio of each in the solutions that are mixed together are not always identical. In some cases, the base is sodium hydroxide, and tin (II) chloride is added as a reducing agent. The exact quantities of each monomer in the solutions that are mixed to precipitate the salt are set out in Table I.

TABLE I

| Sample | DAR (g) | DAR (mmol) | TA (g) | TA (mmol) | Molar Ratio |
|--------|---------|------------|--------|-----------|-------------|
| A | 11.18 | 52.5 | 8.3 | 50 | 1.05:1.0 |
| B | 11.72 | 55 | 8.3 | 50 | 1.10:1.0 |
| C | 10.65 | 50 | 9.13 | 55 | 1.0:1.10 |
| D | 10.65 | 50 | 8.72 | 52.5 | 1.0:1.05 |

The monomer salts are polymerized as described in Example 1, except that the time and temperature are 6 hours at 150° C., 2 hours ramped from 150° C. to 200° C., and 12 hours at 200° C. In each case, the resulting polybenzoxazole polymer has a molecular weight (as determined by gel-phase chromatography) equivalent to an intrinsic viscosity of about 40 dL/g.

EXAMPLE 3

Diaminoresorcinol Terephthalate Salt

A 10.64 g quantity of sodium hydroxide is dissolved in water, and 20 g of terephthalic acid is dissolved in the solution at 80° C. The solution is cooled to room temperature. A 25.65 g quantity of 4,6-diaminoresorcinol bis(hydrogen chloride) (DAR) is dissolved in 210.51 g of water containing 0.024 moles of HCl with 0.02 g of tin (II) chloride. The first solution is added to the second dropwise with stirring over 30 minutes. The pH of the resulting mixture is 4–5. The resulting precipitate is filtered and dried in a vacuum oven. The recovery is 96 percent based on the initial DAR. Elemental analysis suggests that the formula of the salt is $C_{14}H_{14}N_2O_6$. Infrared spectroscopy suggests the existence of some linkage between the diaminoresorcinol and the terephthalic acid. Differential scanning calorimetry shows the peaks at 227° C. and 338° C.

EXAMPLE 4

Diaminoresorcinol Terephthalate Salt

The experiment in Example 3 is repeated, except that the two solutions are mixed at 62° C. and the precipitate is filtered at 30° C. The salt is washed with water and with acetone and dried at 70° C. in a vacuum oven. The recovery is 98.2 percent based upon the initial DAR. Elemental analysis shows 54.66 percent carbon, 4.85 percent hydrogen and 9.12 percent nitrogen by weight. Mass spectroscopy detects only 4,6-diaminoresorcinol and terephthalate ions.

EXAMPLE 5

Rapid Polymerization of Salt

The polymerization process of Example 1 is repeated, except that only 8.73 g of salt is mixed with the solvent and the reaction is carried out for 30 minutes at 75° C. and 3.6 hours at 200° C. A cis-polybenzoxazole polymer is recovered.

EXAMPLE 6

2,5-Diamino-1,4-dithiobenzene Terephthalate Salt

A first solution is made by dissolving 8.31 g of terephthalic acid, and 20 cc of 5 molar sodium hydroxide in 80 cc of water at 90° C. A second solution is made by dissolving 12.25 g of 2,5-diamino-1,4-dithiobenzene bis(hydrogen chloride) (DADTD.2HCl) salt in 200 cc of water under nitrogen atmosphere. The second solution is added dropwise to the first over a period of about 10 minutes. The DADTD-terephthalate salt precipitates and is filtered and washed with deionized water. The salt is dried at 25° C. under vacuum. It is stable in air at room temperature for several hours.

A 9.64 g quantity of the salt ant 10.6 g of $P_2O_5$ are mixed with 27.9 g of polyphosphoric acid (containing 83.6 weight percent $P_2O_5$ at a temperature of 150° C. The reaction is continued with rigorous agitation for 5 hours at 150° C., for 2 hours ramped from 150° C. to 200° C. and for 12 hours at 200° C. A trans-PBT polymer is recovered having a single point intrinsic viscosity of about 13 dL/g in methanesulfonic acid at 25° C.

EXAMPLE 7

Diaminoresorcinol Terephthalate Salt

A mixture containing 1200 ml of deionized water, 166.1 g of terephthalic acid and 404 g of sodium hydroxide is mixed under nitrogen atmosphere until all solids have dissolved. The mixture is then heated to 85°–90° C., and 213 g of 4,6-diaminoresorcinol bis(hydrogen chloride) is added. The mixture is stirred for 30 minutes and then cooled to about 33° C. A 247.73 g quantity of the above-named salt is recovered by the process described in claim 1.

What is claimed is:

1. A solid AA-PBZ monomer/BB-PBZ monomer salt comprising:
   (1) protonated BB-PBZ monomer cations; and
   (2) anions of an AA-PBZ monomer that contains two electron-deficient carbon groups linked by a divalent organic moiety.

2. The salt of claim 1 wherein the AA-PBZ monomer is represented by the Formula:

Q-DM-Q wherein each Q is a carboxylic acid or carboxylate moiety and DM comprises a single aromatic ring or a multi-ring fused or unfused structure.

3. The salt of claim 2 wherein DM is selected such that the monomer can be polymerized to form lyotropic liquid crystalline polymers.

4. The salt of claim 2 wherein the AA-PBZ monomer is derived from terephthalic acid or 4,4'-bisbenzoic acid.

5. The salt of claim 1 wherein the BB-PBZ monomer is represented by the Formula:

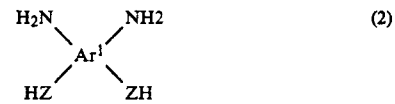

wherein each Z is independently either —O— or —S—.

6. The salt of claim 5 wherein $Ar^1$ is contains a moiety represented by the Formula:

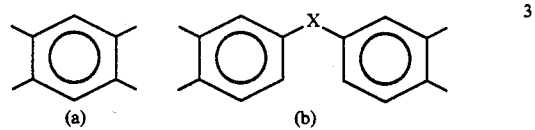

and X is nil, an oxygen atom, a carbonyl group, a sulfonyl group, an alkyl group or a haloalkyl group.

7. The salt of claim 5 wherein the BB-PBZ monomer is 4,6-diaminoresorcinol, 2,5-diaminohydroquinone, 2,4-diamino-1,5-dithiobenzene or 2,5-diamino-1,4-dithiobenzene.

8. The salt of claim 1 wherein the salt contains no more than about 1 weight percent halide ion.

9. The salt of claim 1 wherein neither monomer has a excess of more than about 3 mole percent.

10. The salt of claim 1 wherein the AA-PBZ monomer ion is a terephthalate ion and the BB-PBZ monomer ion is a protonated 4,6-diaminoresorcinol; 2,5--diaminohydroquinone; 2,4-diamino-1,5-dithiobenzene or 2,5-diamino-1,4-dithiobenzene.

11. A process to make an AA-PBZ monomer/BB-PBZ monomer salt comprising the step of contacting an aqueous-soluble AA-PBZ monomer salt with an aqueous soluble BB-PBZ monomer salt in an aqueous solution under conditions such that the AA-PBZ monomer/BB-PBZ monomer salt precipitates.

12. The process of claim 11 wherein the temperature is between 0° C. and 100° C. and the atmosphere is a non-oxidizing atmosphere.

13. The process of claim 12 wherein a first aqueous solution containing between about 0.05 and 1 molar AA-PBZ monomer salt is mixed with a second solution containing between about 0.05 and 1 molar BB-PBZ monomer salt.

14. The process of claim 13 wherein the AA-PBZ monomer is terephthalic acid or 4,4-bisbenzoic acid or a salt thereof; and the BB-PBZ monomer is 4,6-diaminoresorcinol; 2,5-diaminohydroquinone; 2,4-diamino-1,5-dithiobenzene or 2,5-diamino-1,4-dithiobenzene or a salt thereof.

15. A method of using an AA-PBZ monomer/BB-PBZ monomer salt comprising the steps of:
   (1) mixing a salt that contains both AA-PBZ monomer ions and BB-PBZ monomer ions in quantities such that the salt contains no more than about 5 mole percent excess of either monomer with a solvent that is suitable for making polybenzazole polymers to form a polymerization mixture; and
   (2) reacting the monomers in the polymerization mixture under conditions such that a dope containing a polybenzazole polymer is formed.

16. The method of claim 15 wherein the solvent is a dehydrating, non-oxidizing acid solution.

17. The method of claim 16 wherein the solvent is a mixture of methanesulfonic acid with a dehydrating agent.

18. The method of claim 16 wherein the solvent is a polyphosphoric acid that contains at least about 82 weight percent $P_2O_5$ during at least part of Step (2).

19. The method of claim 16 wherein the method proceeds from Step (1) to Step (2) without an intervening devolatilization step.

20. The method of claim 19 wherein the concentration of monomer salt in the reaction mixture is suitable to make a dope containing at least 10 weight percent polymer.

21. The method of claim 16 wherein the molar ratio of AA-PBZ monomer to BB-PBZ monomer in the salt is within about 3 mole percent of 1:1.

22. The method of claim 16 wherein the temperature of the reaction is between about 170° C. and about 230° C. for at least part of the reaction.

23. The method of claim 22 wherein Step (2) commences at a temperature between about 140° C. and about 200° C.

24. The method of claim 16 wherein the AA-PBZ monomer is terephthalic acid or 4,4'-bisbenzoic acid salt; the BB-PBZ monomer is 4,6-diaminoresorcinol; 2,5-diaminohydroquinone; 2,4-diamino-1,5-dithiobenzene or 2,5-diamino-1,4-dithiobenzene; the solvent is a polyphosphoric acid that contains at least about 82 weight percent $P_2O_5$ at the commencement of Step (2); and the concentration of monomer salt in the solvent is suitable to provide a liquid crystalline dope at the completion of Step (2).

* * * * *